(12) United States Patent
Bhaumik et al.

(10) Patent No.: US 8,299,354 B2
(45) Date of Patent: Oct. 30, 2012

(54) LUMINESCENT SOLAR COLLECTOR

(75) Inventors: Kankan Bhaumik, Wesr Bengal (IN); Jeremy D. Hurst, Rotterdam (NL); Pradeep Jeevaji Nadkarni, Bangalore (IN); Nedumbamana Sankaran, Bangalore (IN); Suresh Velate, Bangalore (IN)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 248 days.

(21) Appl. No.: 12/194,136

(22) Filed: Aug. 19, 2008

(65) Prior Publication Data
US 2010/0043879 A1 Feb. 25, 2010

(51) Int. Cl.
H01L 31/00 (2006.01)
C07D 471/00 (2006.01)
(52) U.S. Cl. .......................... 136/257; 546/27
(58) Field of Classification Search .................. 546/37, 546/27, 34; 252/299.1, 299.61, 301.26; 430/78, 430/58.6; 106/498; 438/99; 544/245; 257/40; 136/257
See application file for complete search history.

(56) References Cited

U.S. PATENT DOCUMENTS

| | | | |
|---|---|---|---|
| 4,110,123 A | 8/1978 | Goetzberger et al. | |
| 4,227,939 A | 10/1980 | Zewail et al. | |
| 4,336,383 A | 6/1982 | Verozhtsov et al. | |
| 4,367,367 A | 1/1983 | Reisfeld et al. | |
| 4,395,582 A | 7/1983 | Damsker | |
| 4,415,685 A | 11/1983 | Iqbal et al. | |
| 4,446,324 A | 5/1984 | Graser | |
| 4,486,587 A | 12/1984 | Seybold | |
| 4,618,694 A | 10/1986 | Iden et al. | |
| 4,661,649 A | 4/1987 | Reisfeld et al. | |
| 4,845,223 A | 7/1989 | Seybold et al. | |
| 5,650,513 A | 7/1997 | Langhals et al. | |
| 5,674,622 A | 10/1997 | Burns et al. | |
| 5,816,238 A | 10/1998 | Burns et al. | |
| 5,900,490 A | 5/1999 | Feiler | |
| 5,920,429 A | 7/1999 | Burns et al. | |
| 5,981,773 A | 11/1999 | Langhals et al. | |
| 6,136,976 A | 10/2000 | Böehm et al. | |
| 6,806,368 B2 * | 10/2004 | Wurthner et al. | 546/37 |
| 2002/0074035 A1 | 6/2002 | Gravisse et al. | |
| 2005/0075453 A1 | 4/2005 | Mathauer et al. | |
| 2008/0017850 A1 * | 1/2008 | Koenemann et al. | 257/40 |
| 2008/0114170 A1 | 5/2008 | Konemann et al. | |

FOREIGN PATENT DOCUMENTS

| | | |
|---|---|---|
| EP | 0041274 B1 | 3/1984 |
| EP | 0073007 B1 | 12/1984 |
| EP | 0847599 B1 | 1/2002 |
| JP | 11067450 | 3/1999 |
| WO | 2007031446 A2 | 3/2007 |
| WO | 2007035466 A2 | 3/2007 |

OTHER PUBLICATIONS

BASF Corporation, Lumogen(R) F Orange 240, Colorants & Additives for Plastics.
BASF Corporation, Lumogen(R) F Red 300, Colorants & Additives for Plastics.

* cited by examiner

Primary Examiner — Ling Choi
Assistant Examiner — Monique Peets
(74) Attorney, Agent, or Firm — Richard M. Klein; Fay Sharpe LLP

(57) ABSTRACT

Disclosed are fluorescent dye compounds of Formula (I) or (II):

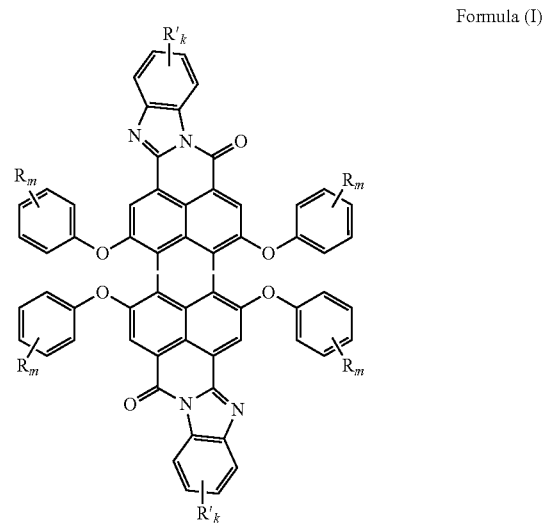

Formula (I)

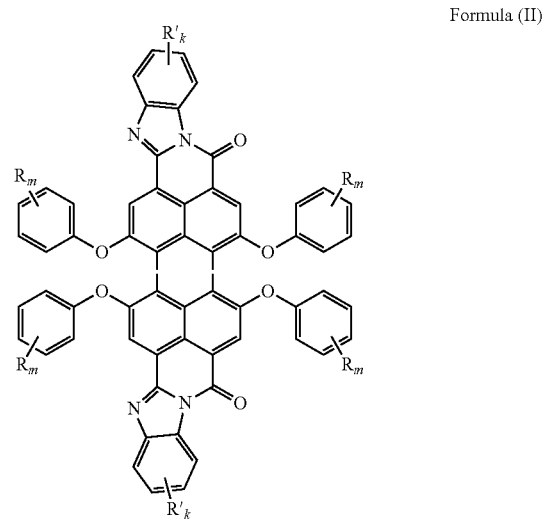

Formula (II)

where R, R', m and k are as described herein. The dye compounds are suitable for use in luminescent solar collectors. Methods of making the dye compounds and luminescent solar collectors comprising them are also described.

7 Claims, 2 Drawing Sheets

LUMINESCENT SOLAR COLLECTOR

CROSS-REFERENCE TO RELATED APPLICATIONS

This application is related to Ser. No. 12/194,008 entitled "LUMINESCENT SOLAR COLLECTOR" and filed on Aug. 19, 2008; Ser. No. 12/194,097 entitled "LUMINESCENT SOLAR COLLECTOR" and filed on Aug. 19, 2008; and Ser. No. 12/194,199 entitled "LUMINESCENT SOLAR COLLECTOR" and filed on Aug. 19, 2008. These three related applications are hereby incorporated by reference in their entirety.

BACKGROUND

The present disclosure generally relates to luminescent solar collectors. In particular, it relates to methods of increasing the concentration of light at the edge of such a solar collector.

Luminescent solar collectors (LSCs), or luminescent solar concentrators, are beneficial for capturing solar energy for use. An LSC usually comprises a sheet, generally a molded polymer, having a surface area. Dispersed, dissolved, or doped within the sheet is a fluorescent dye. When the sheet is exposed to light (radiation energy), the dye absorbs a portion of the light and emits the absorbed light energy at different, longer wavelengths. This light is then transported, via total internal reflection, to at least one edge of the sheet. The concentration of light from a large surface area to a smaller surface area (the edge) is also known as the "edge glow" effect. Due to this effect, the amount of light (i.e. energy) available at the edge is related to the total surface area of the sheet. A light energy converter, such as a silicon photocell, can be attached to at least one edge of the LSC to convert the light energy transmitted thereto into electricity. This enables the LSC to concentrate the maximum amount of light at its edge or edges to generate more electrical power.

The amount of light (i.e. energy) available at the edge is related to the total amount of incident light contacting the sheet; the type of polymer matrix; and the absorption and emission efficiencies (i.e. quantum yield) of the fluorescent dye. In summary, the edge emission is related to the total amount of light contacting the sheet which is absorbed by a dye and eventually directed to the edge. Current LSC systems harvest only a limited portion of the light which contacts the sheet because long wavelengths of 600 nanometers and greater are not absorbed and/or the fluorescent dye has a low quantum yield (i.e. below 80%). A high quantum yield is desirable because light lost during fluorescence is also lost to the light energy converter. It is also desirable to collect as much of the light energy on the sheet as possible to produce more unit power per area on the LSC.

BRIEF DESCRIPTION

Disclosed, in various embodiments, are fluorescent dyes suitable for use in luminescent solar collectors, methods for making such dye compounds, and luminescent solar collectors comprising such compounds. These luminescent solar collectors harvest portions of the visible light spectrum which are otherwise lost.

Disclosed are fluorescent dyes of Formula (I) or (II):

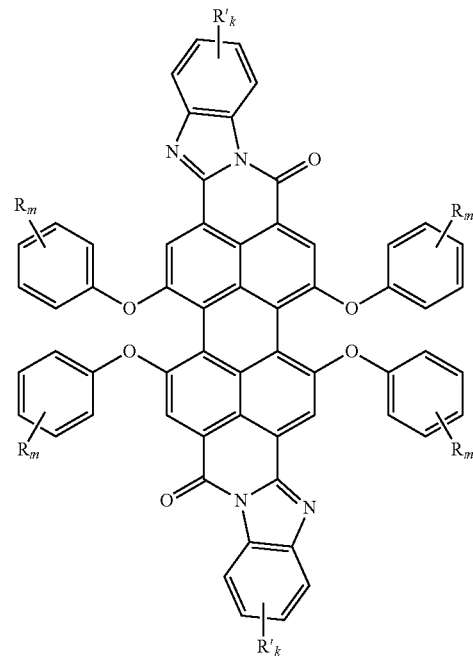

Formula (I)

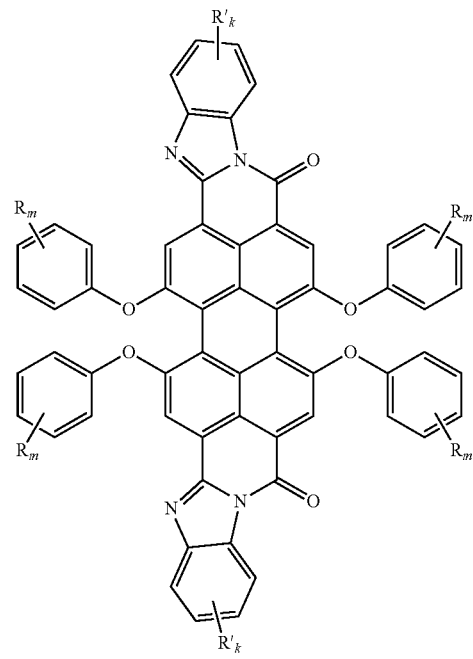

Formula (II)

wherein each R and R' is independently selected from $C_8$-$C_{18}$ alkyl, substituted $C_8$-$C_{18}$ alkyl, $C_8$-$C_{18}$ alkoxy, substituted $C_8$-$C_{18}$ alkoxy, and halogen; m represents the number of R substitutents on each phenoxy ring, wherein each m is independently an integer from 0 to 5; and k represents the number of R' substitutents on each benzimidazole group, wherein each k is independently an integer from 0 to 4.

In specific embodiments, each phenoxy ring is substituted in only the para position with an R group independently selected from $C_8$-$C_{18}$ alkyl. The four R groups in the para position may be the same.

The fluorescent dye may have a quantum yield of about 80% or greater, including 90% or greater and 95% or greater.

The fluorescent dye may have a maximum absorption wavelength of from about 600 nm to 650 nm and a maximum emission wavelength of 650 nm or greater.

Specific fluorescent dyes of Formula (I) or (II) include those of Formulas (III) through (VI) as described further below.

In other embodiments, a solar collector is disclosed which comprises a sheet and a light energy converter operatively connected to the sheet;

the sheet comprising a thermoplastic polymer and a fluorescent dye of Formula (I) or (II) dispersed therein, wherein each R and R' is independently selected from $C_1$-$C_{18}$ alkyl, substituted $C_1$-$C_{18}$ alkyl, $C_1$-$C_{18}$ alkoxy, substituted $C_1$-$C_{18}$ alkoxy, and halogen; each m is independently an integer from 0 to 5; and each k is independently an integer from 0 to 4; and wherein the fluorescent dye absorbs light and radiates the absorbed light at a longer wavelength, and the sheet is configured to transmit the radiated light to the light energy converter; wherein the sheet has an edge emission output of about 150 $W/m^2$ or greater when measured using a sheet of dimensions 60 mm×60 mm×3.2 mm and exposed to a radiation intensity of about 1000 $W/m^2$.

The fluorescent dye may be present in an amount of from about 0.001 to about 1.0 weight percent, based on the total weight of the sheet. The thermoplastic polymer may be a polycarbonate polymer or polymethyl methacrylate. The fluorescent dye may be that of Formula (III), (IV), (V), (VI), (VII), or (VIII), as described further below.

A method of forming a fluorescent dye of Formula (I) or (II) is also disclosed, the method comprising:

condensing a tetrachloroperylene dianhydride with an o-phenylene diamine to form an intermediate; and reacting the intermediate with a base and a phenol of Formula (IX), as described further below, in an aprotic polar solvent to form the fluorescent dye of Formula (I) or (II).

The condensing step may be performed at a temperature of from about 80° C. to about 200° C. The condensing step may be performed over a time period of from about 3 hours to about 12 hours. The condensing step may be performed in an organic solvent, such as propionic acid, acetic acid, imidazole, quinoline, isoquinoline, N-methylpyrrolidone, dimethylformamide, and halogenated solvents.

The reacting step may be performed at a temperature of from about 80° C. to about 200° C. The reacting step may be performed over a time period of from about 4 hours to about 36 hours. The base may comprise sodium or potassium. The aprotic polar solvent may be dimethylformamide, n-methylpyrrolidone, dimethyl sulfoxide, or dimethylacetamide.

These and other non-limiting characteristics of the luminescent solar collectors of the present disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
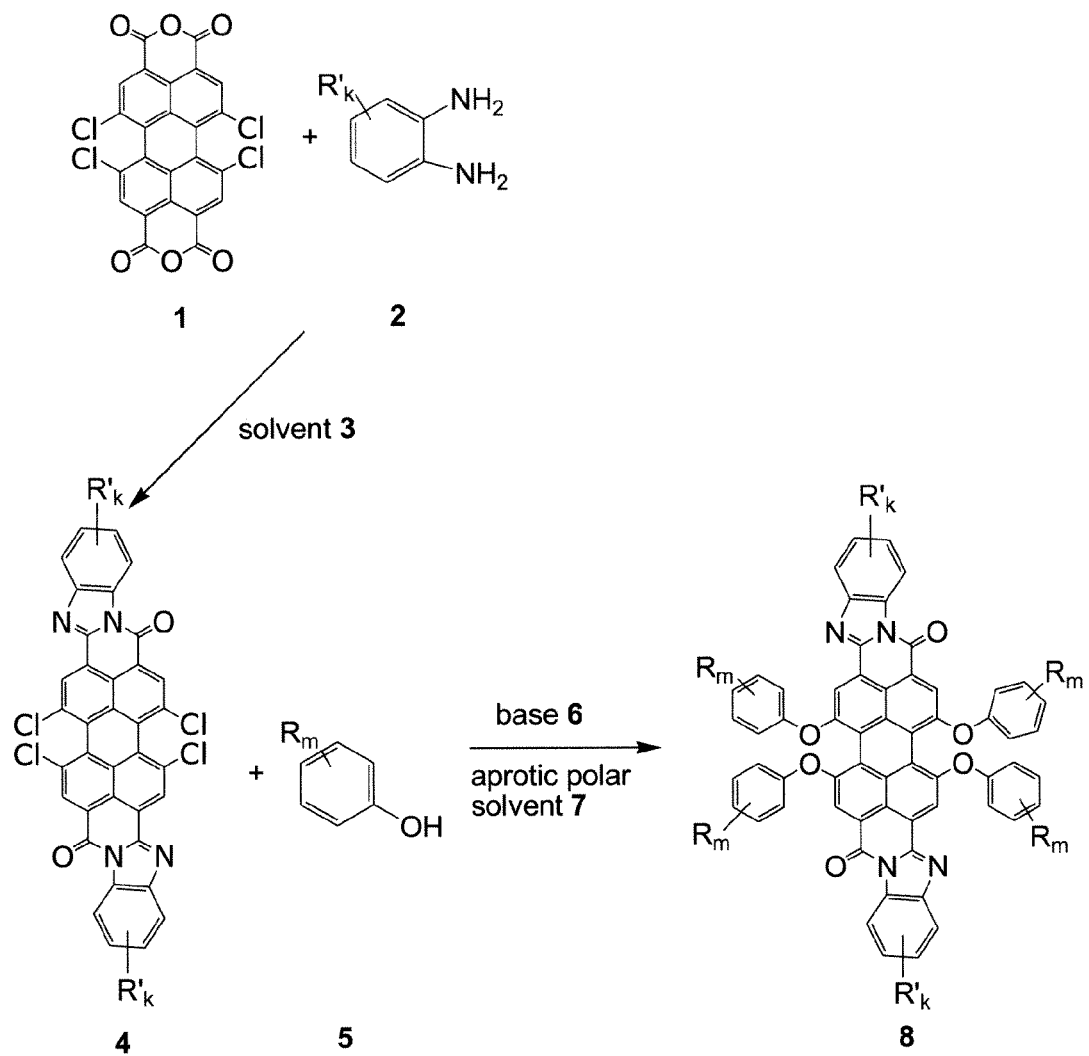
FIG. 1 is a diagram of a process for synthesizing dye compounds of the present disclosure.

A more complete understanding of the components, processes and apparatuses disclosed herein can be obtained by reference to the accompanying drawings. These drawings are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Numerical values in the specification and claims of this application, particularly as they relate to polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise. All ranges disclosed herein are inclusive of the recited endpoint and independently combinable (for example, the range of "from 2 grams to 10 grams" is inclusive of the endpoints, 2 grams and 10 grams, and all the intermediate values).

The modifier "about" used in connection with a quantity is inclusive of the stated value and has the meaning dictated by the context (for example, it includes at least the degree of error associated with the measurement of the particular quantity).

The term "integer" means a whole number and includes zero. For example, the expression "n is an integer from 0 to 4" means n may be any whole number from 0 to 4, including 0.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, the aldehyde group —CHO is attached through the carbon of the carbonyl group.

The term "aliphatic" refers to a linear or branched array of atoms that is not cyclic and has a valence of at least one. Aliphatic groups are defined to comprise at least one carbon atom. The array of atoms may include heteroatoms such as nitrogen, sulfur, silicon, selenium and oxygen or may be composed exclusively of carbon and hydrogen ("Alkyl"). Aliphatic groups may be substituted or unsubstituted. Exemplary aliphatic groups include, but are not limited to, methyl, ethyl, isopropyl, isobutyl, chloromethyl, hydroxymethyl (—$CH_2OH$), mercaptomethyl (—$CH_2SH$), methoxy, methoxycarbonyl ($CH_3OCO$—), nitromethyl (—$CH_2NO_2$), and thiocarbonyl.

The term "alkyl" refers to a linear or branched array of atoms that is composed exclusively of carbon and hydrogen. The array of atoms may include single bonds, double bonds, or triple bonds (typically referred to as alkane, alkene, or alkyne). Alkyl groups may be substituted or unsubstituted. Exemplary alkyl groups include, but are not limited to, methyl, ethyl, and isopropyl.

The term "aromatic" refers to an array of atoms having a valence of at least one and comprising at least one aromatic group. The array of atoms may include heteroatoms such as nitrogen, sulfur, selenium, silicon and oxygen, or may be composed exclusively of carbon and hydrogen. The aromatic group may also include nonaromatic components. For example, a benzyl group is an aromatic group that comprises a phenyl ring (the aromatic component) and a methylene group (the nonaromatic component). Exemplary aromatic groups include, but are not limited to, phenyl, pyridyl, furanyl, thienyl, naphthyl, biphenyl, 4-trifluoromethylphenyl, 4-chloromethylphen-1-yl, and 3-trichloromethylphen-1-yl (3-CCl$_3$Ph-).

The terms "cycloaliphatic" and "cycloalkyl" refer to an array of atoms which is cyclic but which is not aromatic. The cycloaliphatic group may include heteroatoms such as nitrogen, sulfur, selenium, silicon and oxygen, or may be composed exclusively of carbon and hydrogen. A cycloalkyl group is composed exclusively of carbon and hydrogen. A cycloaliphatic group may comprise one or more noncyclic components. For example, a cyclohexylmethyl group (C$_6$H$_{11}$CH$_2$) is a cycloaliphatic functionality, which comprises a cyclohexyl ring (the array of atoms which is cyclic but which is not aromatic) and a methylene group (the noncyclic component). Exemplary cycloaliphatic groups include, but are not limited to, cyclopropyl, cyclobutyl, 1,1,4,4-tetramethylcyclobutyl, piperidinyl, and 2,2,6,6-tetramethylpiperydinyl.

The term "alkoxy" refers to an array of atoms containing an alkyl group and an oxygen atom at one end. Alkyl groups may be substituted or unsubstituted. Exemplary alkoxy groups include methoxy(—OCH$_3$) and ethoxy(—OCH$_2$CH$_3$). A related group is "phenoxy," which refers to a phenyl group having an oxygen atom attached to one carbon. The phenoxy group may also be substituted or unsubstituted.

The present application discloses a dye compound of Formula (I) or (II):

Formula (I)

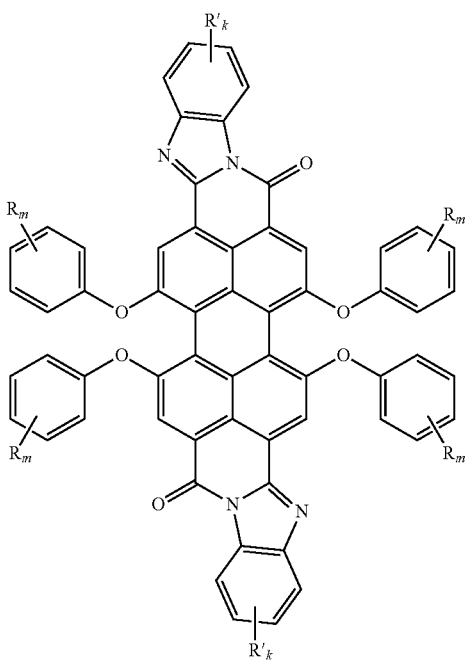

Formula (II)

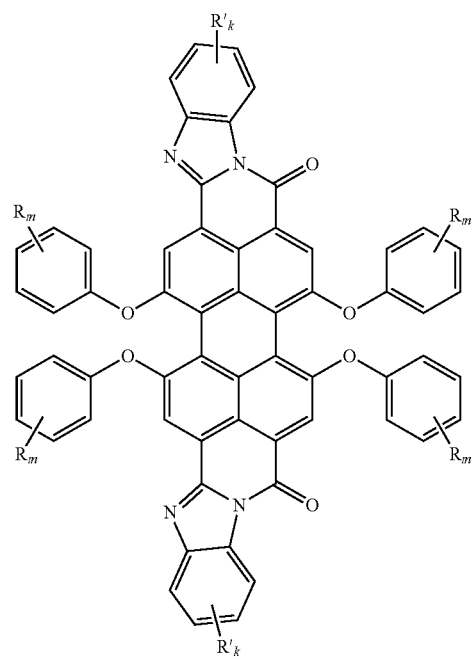

wherein each R and R' is independently selected from C$_1$-C$_{18}$ alkyl, substituted C$_1$-C$_{18}$ alkyl, C$_1$-C$_{18}$ alkoxy, substituted C$_1$-C$_{18}$ alkoxy, and halogen; m represents the number of R substitutents on each phenoxy ring, wherein each m is independently an integer from 0 to 5; and k represents the number of R' substitutents on each benzimidazole group, wherein each k is independently an integer from 0 to 4. The compounds can be considered as having a perylene core, two benzimidazole end groups (trans and cis isomers), and four phenoxy side groups. The hydrogen atoms of the alkyl and alkoxy groups may be substituted with, for example, hydroxyl and phenyl groups.

In some specific embodiments, each phenoxy group is substituted in only the para position with an R group independently selected from C$_8$-C$_{18}$ alkyl (with respect to the oxygen atom) (i.e. m=1). In more specific embodiments, the four R groups in the para position are the same. In other specific embodiments, each k is zero.

In particular embodiments, each R and R' is independently selected from C$_8$-C$_{18}$ alkyl, substituted C$_8$-C$_{18}$ alkyl, C$_8$-C$_{18}$ alkoxy, substituted C$_8$-C$_{18}$ alkoxy, and halogen; each m is independently an integer from 0 to 5; and each k is independently an integer from 0 to 4.

Exemplary compounds include those of Formulas (III) through (VIII):

Formula (III)
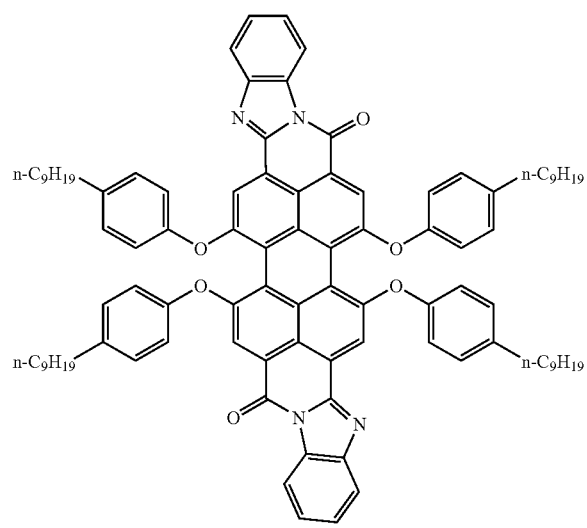
Formula (IV)
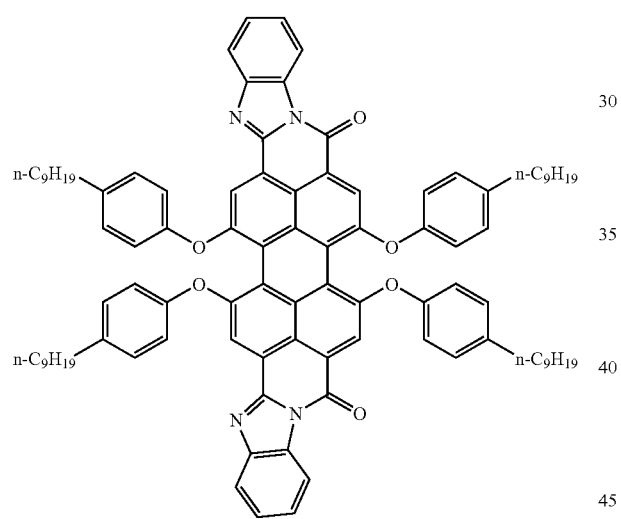
Formula (V)
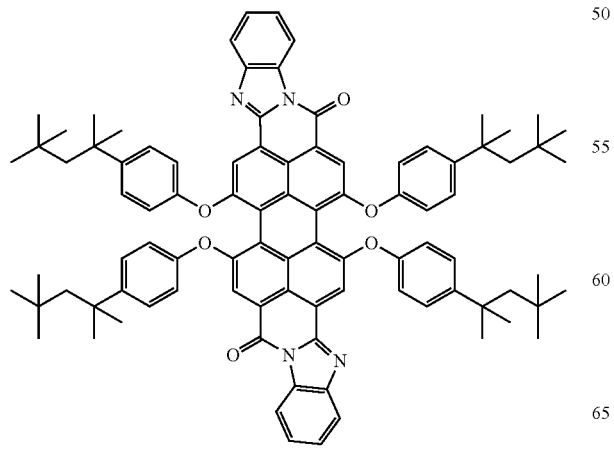
Formula (VI)
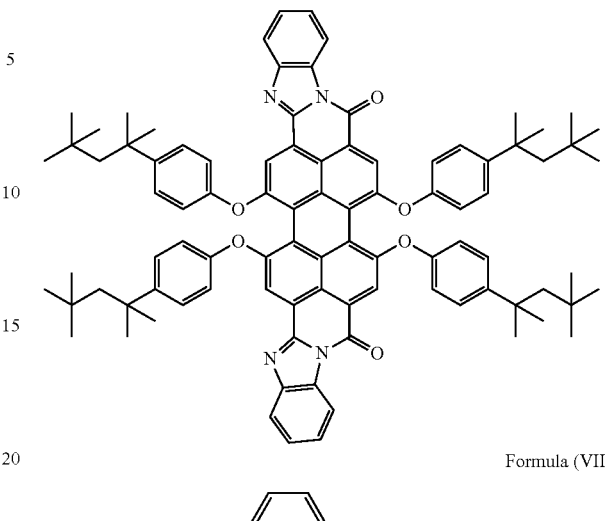
Formula (VII)
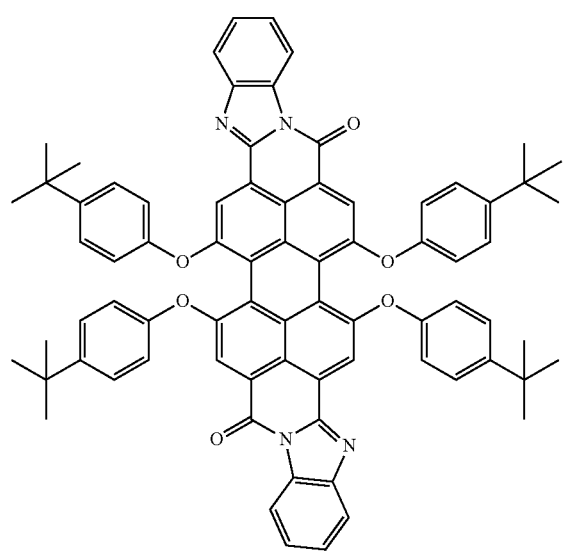
Formula (VIII)
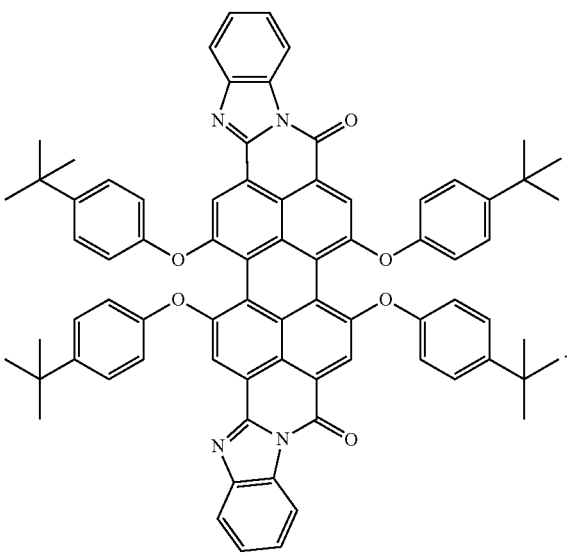
The compounds of Formula (I) and (II) generally have a maximum absorption wavelength of from about 600 nanometers to 650 nanometers, and a maximum emission wavelength of 650 nanometers or greater. They may also have a quantum yield of about 80% or greater, including 90% or greater and 95% or greater.

An exemplary diagram showing the synthesis of the dye compounds of Formula (I) and (II) is shown in FIG. 1. The dye compounds of Formulas (I) and (II) can be synthesized by condensing a tetrachloroperylene dianhydride 1 with an o-phenylene diamine 2 in an appropriate solvent 3. The intermediate product 4 formed from the reaction of the tetrachloroperylene dianhydride and o-phenylene diamine can be used without purification or separation. The intermediate product is then reacted with a base 5 and a phenol 6 in an aprotic polar solvent 7 to obtain the dye compound 8 of Formula (I) or (II) (here, only Formula (I) is shown).

The o-phenylene diamine (also known as diaminobenzene) is used to form the benzimidazole end groups of the dye compound. If desired, substituted o-phenylene diamines may also be used. The o-phenylene diamines may be substituted with $C_1$-$C_{18}$ alkyl, substituted $C_1$-$C_{18}$ alkyl, $C_1$-$C_{18}$ alkoxy, substituted $C_1$-$C_{18}$ alkoxy, and halogen.

Appropriate solvents for the condensation of the tetrachloroperylene dianhydride and o-phenylene diamine include propionic acid, acetic acid, imidazole, quinoline, isoquinoline, N-methylpyrrolidone, dimethylformamide, and halogenated solvents like o-dichlorobenzene.

The phenol reacts with the base to form a phenol salt that more easily reacts with the intermediate product. In specific embodiments, the base is a potassium or sodium base. Exemplary bases include potassium carbonate ($K_2CO_3$), sodium carbonate, and similar bases. Especially desirable are bases having a pKa of 10 or less.

The phenol used to react with the intermediate product generally has the structure of Formula (IX):

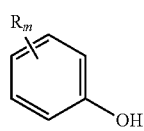

Formula (IX)

where R and m are as described above. Exemplary phenols include nonyl phenol; p-tert-butyl phenol; and p-tert-octyl phenol.

Suitable aprotic polar solvents include dimethylformamide (DMF); n-methyl pyrrolidone (NMP); dimethyl sulfoxide (DMSO); dimethylacetamide; and halogenated solvents like o-dichlorobenzene.

The condensing reaction of the tetrachloroperylene dianhydride and o-phenylene diamine can be performed at temperatures of from about 80° C. to about 200° C. The condensing reaction may take place over a time period of from about 3 hours to about 12 hours, including from about 4 hours to about 8 hours.

The reaction of the intermediate product with the base and the phenol can be performed at temperatures of from about 80° C. to about 200° C. In more specific embodiments, the temperature is from about 130° C. to about 160° C. The condensing reaction may take place over a time period of from about 4 hours to about 36 hours. In more specific embodiments, the time period is from about 4 hours to about 28 hours. The reaction of the intermediate product with the base and the phenol may also take place in an inert atmosphere, such as under nitrogen or argon gas. Desirably, the solvent is "dry", i.e. contains as little water as possible.

After the dye compound of Formula (I) or (II) is formed, it may be purified by column chromatography. The dye compounds are soluble in common solvents like chlorobenzene, dichlorobenzene, toluene, chloroform, and dichloromethane. The dye compound of Formula (I) or (II) is particularly useful as a fluorescent dye in a luminescent solar collector (LSC).

Figure 2:
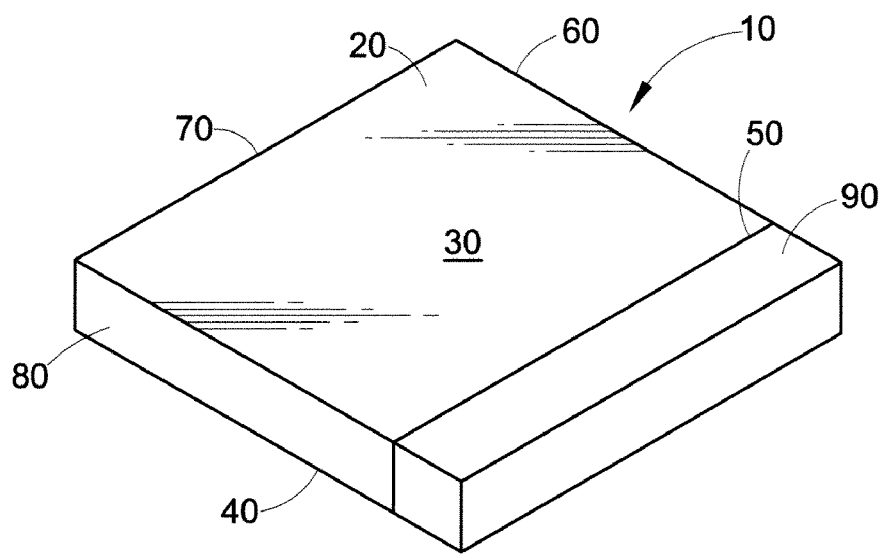
FIG. 2 is an elevated view of a luminescent solar collector.
Figure 3:
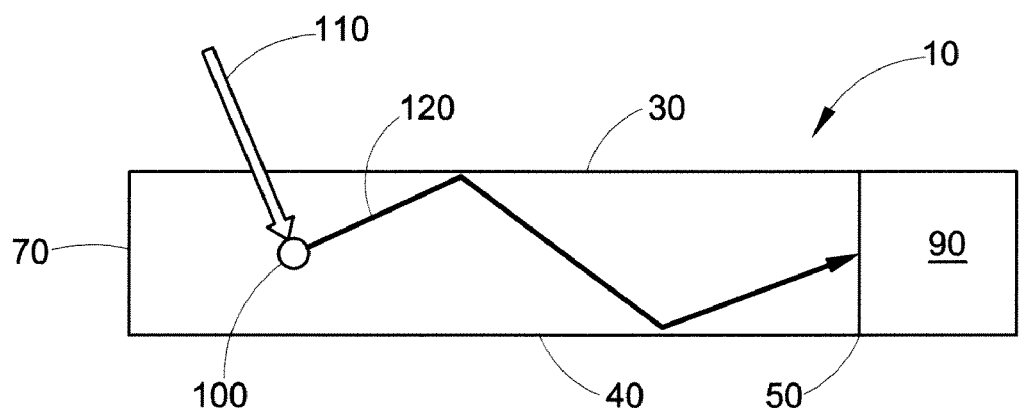
FIG. 3 is a side view of a first exemplary embodiment of the luminescent solar collector.

Referring to FIGS. 2 and 3, a luminescent solar collector (LSC) 10 comprises a sheet (or panel) 20. The sheet or panel has two opposing surfaces 30, 40. The opposing surfaces 30, 40 are joined by at least one edge 50. For the sheet depicted, there are three additional connecting edges 60, 70, 80. The sheet comprises a thermoplastic polymer and fluorescent dye molecules 100 dispersed evenly therein. A light energy converter, such as a photocell 90, is mounted or operatively connected to the at least one connecting edge 50 to convert the light to electricity. For example, the operative connection may be made by means including, but not limited to, glueing the converter to the edge, mounting it in a slit, or by positioning it along the edge. Edge emission may be measured in watts per square meter ($W/m^2$). It is measured where the operative connection to the light energy converter is made. In this embodiment, the edge emission is measured is at the connecting edge 50. The area in the denominator is that of the edge 50, not that of the surface 30.

As explained above, light 110 is absorbed by the fluorescent dye molecules 100. The molecules 100 then emit light 120 with a Stokes shift (i.e. towards a higher wavelength). The emitted light, due to total internal reflection, is guided towards the edge 50 of the sheet where the photocell 90 is located. The other edges 60, 70, 80 may be coated, for example with a mirror coating to reflect light towards edge 50 as well. An opposing surface 40 may also be coated to reflect light as well.

The sheet 20 is wide in two dimensions and thinner in the third dimension (its thickness). The opposing surfaces 30, 40 of the sheet 20 are generally parallel to each other, but need not be. It is also contemplated that the sheet 20 may be molded into various shapes. For example, the sheet may have the shape of a pyramidal frustum, a box, or as the surface of a hemisphere. The sheet may also vary in thickness. In particular embodiments, the sheet is planar. This shape is contemplated for use, for example, on the side or rooftop of a building, such as a house.

The sheet of the LSC comprises a thermoplastic polymer and a fluorescent dye. Types of thermoplastic polymers that are useful comprise polycarbonates, including homopolycarbonates, copolycarbonates, polyester-polycarbonates, and polysiloxane-polycarbonates; polyesters including poly (alkylene terephthalate); polyetherimides; polysiloxane-polyetherimides; polyphenylene ethers; polyolefins; addition polymers, including homopolymers and copolymers, especially homopolymers of alkenylaromatic compounds, such as polystyrenes, and copolymers of alkenylaromatic compounds, such as impact modified poly(alkenylaromatic) copolymers with ethylenically unsaturated nitriles, and poly (meth)acrylates, particularly polymethyl methacrylate.

In particular embodiments, the thermoplastic polymer is a polycarbonate. As used herein, the terms "polycarbonate" and "polycarbonate resin" mean compositions having repeating structural carbonate units of the formula (1):

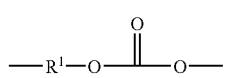
(1)

in which at least 60 percent of the total number of $R^1$ groups are aromatic organic radicals and the balance thereof are aliphatic, alicyclic, or aromatic radicals. In one embodiment, each $R^1$ is an aromatic organic radical, for example a radical of the formula (2):

$$-A^1-Y^1-A^2- \qquad (2)$$

wherein each of $A^1$ and $A^2$ is a monocyclic divalent aryl radical and $Y^1$ is a bridging radical having one or two atoms that separate $A^1$ from $A^2$. In an exemplary embodiment, one atom separates $A^1$ from $A^2$. Illustrative non-limiting examples of radicals of this type are —O—, —S—, —S(O)—, —S(O)$_2$—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ may be a hydrocarbon group or a saturated hydrocarbon group such as methylene, cyclohexylidene, or isopropylidene.

Polycarbonates may be produced by the interfacial reaction of dihydroxy compounds having the formula HO—$R^1$—OH, which includes dihydroxy compounds of formula (3)

$$\text{HO-}A^1\text{-}Y^1\text{-}A^2\text{-OH} \tag{3}$$

wherein $Y^1$, $A^1$ and $A^2$ are as described above. Also included are bisphenol compounds of general formula (4):

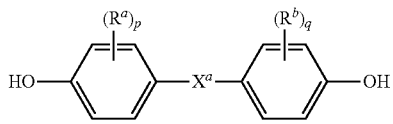

(4)

wherein $R^a$ and $R^b$ each represent a halogen atom or a monovalent hydrocarbon group and may be the same or different; p and q are each independently integers of 0 to 4; and $X^a$ represents one of the groups of formula (5):

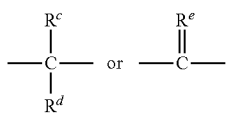

(5)

wherein $R^c$ and $R^d$ each independently represent a hydrogen atom or a monovalent linear or cyclic hydrocarbon group and $R^e$ is a divalent hydrocarbon group.

In an embodiment, a heteroatom-containing cyclic alkylidene group comprises at least one heteroatom with a valency of 2 or greater, and at least two carbon atoms. Heteroatoms for use in the heteroatom-containing cyclic alkylidene group include —O—, —S—, and —N(Z)—, where Z is a substituent group selected from hydrogen, hydroxy, $C_{1-12}$ alkyl, $C_{1-12}$ alkoxy, or $C_{1-12}$ acyl. Where present, the cyclic alkylidene group or heteroatom-containing cyclic alkylidene group may have 3 to 20 atoms, and may be a single saturated or unsaturated ring, or fused polycyclic ring system wherein the fused rings are saturated, unsaturated, or aromatic.

Other bisphenols containing substituted or unsubstituted cyclohexane units can be used, for example bisphenols of formula (6):

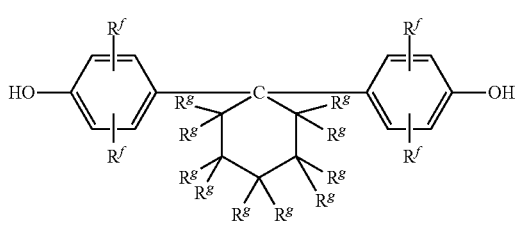

(6)

wherein each $R^f$ is independently hydrogen, $C_{1-12}$ alkyl, or halogen; and each $R^g$ is independently hydrogen or $C_{1-12}$ alkyl. The substituents may be aliphatic or aromatic, straight chain, cyclic, bicyclic, branched, saturated, or unsaturated. Such cyclohexane-containing bisphenols, for example the reaction product of two moles of a phenol with one mole of a hydrogenated isophorone, are useful for making polycarbonate polymers with high glass transition temperatures and high heat distortion temperatures. Cyclohexyl bisphenol containing polycarbonates, or a combination comprising at least one of the foregoing with other bisphenol polycarbonates, are supplied by Bayer Co. under the APEC® trade name.

Other useful dihydroxy compounds having the formula HO—$R^1$—OH include aromatic dihydroxy compounds of formula (7):

(7)

wherein each $R^h$ is independently a halogen atom, a $C_{1-10}$ hydrocarbyl such as a $C_{1-10}$ alkyl group, a halogen substituted $C_{1-10}$ hydrocarbyl such as a halogen-substituted $C_{1-10}$ alkyl group, and n is 0 to 4. The halogen is usually bromine.

Specific examples of bisphenol compounds that may be represented by formula (3) include 1,1-bis(4-hydroxyphenyl) methane, 1,1-bis(4-hydroxyphenyl)ethane, 2,2-bis(4-hydroxyphenyl)propane (hereinafter "bisphenol-A" or "BPA"), 2,2-bis(4-hydroxyphenyl)butane, 2,2-bis(4-hydroxyphenyl) octane, 1,1-bis(4-hydroxyphenyl)propane, 1,1-bis(4-hydroxyphenyl)n-butane, 2,2-bis(4-hydroxy-1-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl)phthalimidine (PPPBP), and 1,1-bis(4-hydroxy-3-methylphenyl)cyclohexane (DMBPC). Combinations comprising at least one of the foregoing dihydroxy compounds may also be used.

In a specific embodiment, the polycarbonate is a linear homopolymer derived from bisphenol-A, in which each of $A^1$ and $A^2$ is p-phenylene and $Y^1$ is isopropylidene. The polycarbonates may have an intrinsic viscosity, as determined in chloroform at 25° C., of from about 0.3 to about 1.5 deciliters per gram (dl/g), specifically from about 0.45 to about 1.0 dl/g. The polycarbonates may have a weight average molecular weight (Mw) of from about 10,000 to about 100,000, as measured by gel permeation chromatography (GPC) using a crosslinked styrene-divinyl benzene column, at a sample concentration of 1 milligram per milliliter, and as calibrated with polycarbonate standards.

In an embodiment, the polycarbonate has a melt volume flow rate (often abbreviated MVR). The MVR measures the rate at which a thermoplastic passes vertically through a capillary under a defined weight load. The MVR is measured in cubic cm per 10 minutes (cc/10 min). Polycarbonates useful for the formation of thin articles may have an MVR, measured at 300° C. under a load of 1.2 kg according to ASTM D1238-04, of from about 0.5 to about 80 cubic centimeters per 10 minutes (cc/10 min). In a specific embodiment, a useful polycarbonate composition has an MVR measured at 300° C. under a load of 1.2 kg according to ASTM D1238-04, of from about 0.5 to about 50 cc/10 min, specifically from about 0.5 to about 25 cc/10 min, and more specifically from about 1 to about 15 cc/10 min. Mixtures of polycarbonates of different flow properties may be used to achieve the overall desired flow property.

The polycarbonate may have a light transmittance greater than or equal to about 55%, specifically greater than or equal to about 60% and more specifically greater than or equal to about 70%, as measured using a molded article of 3.2±0.12 millimeters thickness and consisting of the polycarbonate, according to ASTM D1003-00. The polycarbonate may also have a haze less than or equal to about 5%, specifically less than or equal to about 4%, and most specifically less than or equal to about 3%, as measured using a molded article of 3.2±0.12 millimeters thickness and consisting of the polycarbonate, according to ASTM D1003-00.

"Polycarbonates" and "polycarbonate resins" as used herein further include homopolycarbonates, copolymers comprising different $R^1$ moieties in the carbonate (referred to herein as "copolycarbonates"), copolymers comprising carbonate units and other types of polymer units, such as ester units, polysiloxane units, and combinations comprising at least one of homopolycarbonates and copolycarbonates. As used herein, "combination" is inclusive of blends, mixtures, alloys, reaction products, and the like. A specific type of copolymer is a polyester carbonate, also known as a polyester-polycarbonate. Such copolymers further contain, in addition to recurring carbonate chain units of the formula (1), repeating units of formula (8):

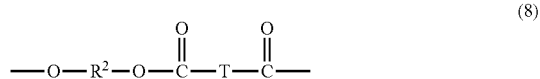

(8)

wherein $R^2$ is a divalent group derived from a dihydroxy compound, and may be, for example, a $C_{2-10}$ alkylene group, a $C_{6-20}$ alicyclic group, a $C_{6-20}$ aromatic group or a polyoxyalkylene group in which the alkylene groups contain 2 to about 6 carbon atoms, specifically 2, 3, or 4 carbon atoms; and T divalent group derived from a dicarboxylic acid, and may be, for example, a $C_{2-10}$ alkylene group, a $C_{6-20}$ alicyclic group, a $C_{6-20}$ alkyl aromatic group, or a $C_{6-20}$ aromatic group.

In an embodiment, $R^2$ is a $C_{2-30}$ alkylene group having a straight chain, branched chain, or cyclic (including polycyclic) structure. In another embodiment, $R^2$ is derived from an aromatic dihydroxy compound of formula (4) above. In another embodiment, $R^2$ is derived from an aromatic dihydroxy compound of formula (7) above.

Polycarbonates can be manufactured by processes such as interfacial polymerization and melt polymerization. Although the reaction conditions for interfacial polymerization may vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a catalyst such as triethylamine or a phase transfer catalyst, under controlled pH conditions, e.g., about 8 to about 10. The most commonly used water immiscible solvents include methylene chloride, 1,2-dichloroethane, chlorobenzene, toluene, and the like.

Carbonate precursors include, for example, a carbonyl halide such as carbonyl bromide or carbonyl chloride, or a haloformate such as a bishaloformates of a dihydric phenol (e.g., the bischloroformates of bisphenol-A, hydroquinone, or the like) or a glycol (e.g., the bishaloformate of ethylene glycol, neopentyl glycol, polyethylene glycol, or the like). Combinations comprising at least one of the foregoing types of carbonate precursors may also be used. In an exemplary embodiment, an interfacial polymerization reaction to form carbonate linkages uses phosgene as a carbonate precursor, and is referred to as a phosgenation reaction.

Among the phase transfer catalysts that may be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Useful phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is Cl$^-$, BR$^-$, a $C_{1-8}$ alkoxy group or a $C_{6-18}$ aryloxy group. An effective amount of a phase transfer catalyst may be about 0.1 to about 10 wt % based on the weight of bisphenol in the phosgenation mixture. In another embodiment an effective amount of phase transfer catalyst may be about 0.5 to about 2 wt % based on the weight of bisphenol in the phosgenation mixture.

Branched polycarbonate blocks may be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bisphenol, tris-phenol TC (1,3,5-tris((p-hydroxyphenyl)isopropyl)benzene), tris-phenol PA (4(4(1,1-bis(p-hydroxyphenyl)-ethyl)alpha,alpha-dimethyl benzyl)phenol), 4-chloroformyl phthalic anhydride, trimesic acid, and benzophenone tetracarboxylic acid. The branching agents may be added at a level of about 0.05 to about 2.0 wt %. Mixtures comprising linear polycarbonates and branched polycarbonates may be used.

A chain stopper (also referred to as a capping agent) may be included during polymerization. The chain stopper controls molecular weight in the polycarbonate. Exemplary chain stoppers include certain mono-phenolic compounds, mono-carboxylic acid chlorides, and/or mono-chloroformates.

Alternatively, melt processes may be used to make the polycarbonates. Generally, in the melt polymerization process, polycarbonates may be prepared by co-reacting, in a molten state, the dihydroxy reactant(s) and a diaryl carbonate ester, such as diphenyl carbonate, in the presence of a transesterification catalyst in a Banbury° mixer, twin screw extruder, or the like to form a uniform dispersion. Volatile monohydric phenol is removed from the molten reactants by distillation and the polymer is isolated as a molten residue. A specifically useful melt process for making polycarbonates uses a diaryl carbonate ester having electron-withdrawing substituents on the aryls. Melt processes are generally carried out in a series of stirred tank reactors. The reaction can be carried out by either a batch mode or a continuous mode. The apparatus in which the reaction is carried out can be any suitable tank, tube, or column. Continuous processes usually involve the use of one or more continuous-stirred tank reactors (CSTRs) and one or more finishing reactors.

Polyester-polycarbonates may also be prepared by interfacial polymerization. Rather than utilizing the dicarboxylic acid per se, it is possible, and sometimes even preferred, to employ the reactive derivatives of the acid, such as the corresponding acid halides, in particular the acid dichlorides and the acid dibromides. Thus, for example instead of using isophthalic acid, terephthalic acid, or a combination comprising at least one of the foregoing, it is possible to employ isophthaloyl dichloride, terephthaloyl dichloride, and a combination comprising at least one of the foregoing.

In addition to the polycarbonates described above, combinations of the polycarbonate with other thermoplastic polymers, for example combinations of homopolycarbonates and/ or polycarbonate copolymers with polyesters, may be used. Useful polyesters may include, for example, polyesters having repeating units of formula (8), which include poly(alkylene dicarboxylates), liquid crystalline polyesters, and polyester copolymers. The polyesters described herein are generally completely miscible with the polycarbonates when blended.

Useful polyesters may include aromatic polyesters, poly(alkylene esters) including poly(alkylene arylates), and poly(cycloalkylene diesters). Aromatic polyesters may have a polyester structure according to formula (8), wherein D and T are each aromatic groups as described hereinabove. Also contemplated are aromatic polyesters with a minor amount, e.g., about 0.5 to about 10 wt %, based on the total weight of the polyester, of units derived from an aliphatic diacid and/or an aliphatic polyol to make copolyesters. Poly(alkylene arylates) may have a polyester structure according to formula (8), wherein T comprises groups derived from aromatic dicarboxylates, cycloaliphatic dicarboxylic acids, or derivatives thereof. Specifically, where T is 1,4-phenylene, the poly(alkylene arylate) is a poly(alkylene terephthalate). Examples of poly(alkylene terephthalates) include poly(ethylene terephthalate) (PET), poly(1,4-butylene terephthalate) (PBT), and poly(propylene terephthalate) (PPT). Also useful are poly(alkylene naphthoates), such as poly(ethylene naphthanoate) (PEN), and poly(butylene naphthanoate) (PBN). A useful poly(cycloalkylene diester) is poly(cyclohexanedimethylene terephthalate) (PCT). Combinations comprising at least one of the foregoing polyesters may also be used.

Copolymers comprising alkylene terephthalate repeating ester units with other ester groups may also be useful. Useful ester units may include different alkylene terephthalate units, which can be present in the polymer chain as individual units, or as blocks of poly(alkylene terephthalates). Specific examples of such copolymers include poly(cyclohexanedimethylene terephthalate)-co-poly(ethylene terephthalate), abbreviated as PETG where the polymer comprises greater than or equal to 50 mol % of poly(ethylene terephthalate), and abbreviated as PCTG where the polymer comprises greater than 50 mol % of poly(1,4-cyclohexanedimethylene terephthalate).

Poly(cycloalkylene diester)s may also include poly(alkylene cyclohexanedicarboxylate)s. Of these, a specific example is poly(1,4-cyclohexane-dimethanol-1,4-cyclohexanedicarboxylate) (PCCD), having recurring units of formula (9):

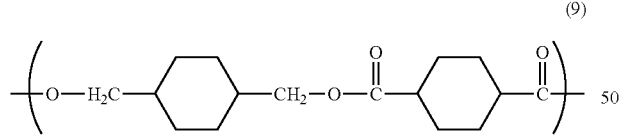

(9)

wherein, as described using formula (8), $R^2$ is a 1,4-cyclohexanedimethylene group derived from 1,4-cyclohexanedimethanol, and T is a cyclohexane ring derived from cyclohexanedicarboxylate or a chemical equivalent thereof, and may comprise the cis-isomer, the trans-isomer, or a combination comprising at least one of the foregoing isomers.

The polyester-polycarbonates may have a weight-average molecular weight ($M_w$) of from about 1,500 to about 100,000, specifically from about 1,700 to about 50,000, and more specifically from about 2,000 to about 40,000. Molecular weight determinations are performed using gel permeation chromatography (GPC), using a crosslinked styrene-divinylbenzene column and calibrated to polycarbonate references. Samples are prepared at a concentration of about 1 mg/ml, and are eluted at a flow rate of about 1.0 ml/min.

Where used, it is desirable for a polyester-polycarbonate to have an MVR of about 5 to about 150 cc/10 min., specifically about 7 to about 125 cc/10 min, more specifically about 9 to about 110 cc/10 min, and still more specifically about 10 to about 100 cc/10 min., measured at 300° C. and a load of 1.2 kilograms according to ASTM D1238-04. Commercial polyester blends with polycarbonate are marketed under the trade name XYLEX®, including for example XYLEX® X7300, and commercial polyester-polycarbonates are marketed under the tradename LEXAN® SLX polymers, including for example LEXAN® SLX-9000, and are available from SABIC Innovative Plastics.

The polycarbonate may also be a polysiloxane-polycarbonate copolymer, also referred to as a polysiloxane-polycarbonate. The polysiloxane (also referred to herein as "polydiorganosiloxane") blocks of the copolymer comprise repeating siloxane units (also referred to herein as "diorganosiloxane units") of formula (10):

(10)

wherein each occurrence of R is same or different, and is a $C_{1-13}$ monovalent organic radical. For example, R may independently be a $C_1$-$C_{13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{14}$ aryl group, $C_6$-$C_{10}$ aryloxy group, $C_7$-$C_{13}$ arylalkyl group, $C_7$-$C_{13}$ arylalkoxy group, $C_7$-$C_{13}$ alkylaryl group, or $C_7$-$C_{13}$ alkylaryloxy group. The foregoing groups may be fully or partially halogenated with fluorine, chlorine, bromine, or iodine, or a combination thereof. Combinations of the foregoing R groups may be used in the same copolymer.

The value of D in formula (10) may vary widely depending on the type and relative amount of each component in the polymer, the desired properties of the polymer, and like considerations. Generally, D may have an average value of 2 to 1,000, specifically 2 to 500, and more specifically 5 to 100. Where D is of a lower value, e.g., less than 40, it may be desirable to use a relatively larger amount of the polycarbonate-polysiloxane copolymer. Conversely, where D is of a higher value, e.g., greater than 40, it may be necessary to use a relatively lower amount of the polycarbonate-polysiloxane copolymer.

In one embodiment, the polydiorganosiloxane blocks are provided by repeating structural units of formula (11):

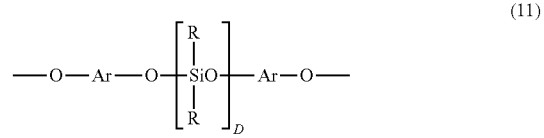

(11)

wherein D is as defined above; each R may independently be the same or different, and is as defined above; and each Ar may independently be the same or different, and is a substituted or unsubstituted $C_6$-$C_{30}$ arylene radical, wherein the bonds are directly connected to an aromatic moiety. Useful Ar groups in formula (11) may be derived from a $C_6$-$C_{30}$ dihydroxyarylene compound, for example a dihydroxyarylene compound of formula (3), (4), or (7) above. Combinations comprising at least one of the foregoing dihydroxyarylene compounds may also be used.

Units of formula (11) may be derived from the corresponding dihydroxy compound of formula (12):

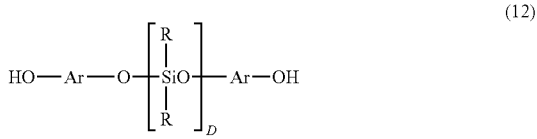

(12)

wherein R, Ar, and D are as described above. Compounds of formula (12) may be obtained by the reaction of a dihydroxyarylene compound with, for example, an alpha, omega-bisacetoxypolydiorganosiloxane under phase transfer conditions.

In another embodiment, polydiorganosiloxane blocks comprise units of formula (13):

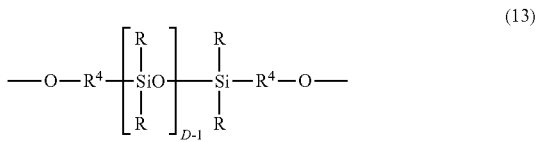

(13)

wherein R and D are as described above, and each occurrence of $R^4$ is independently a divalent $C_1$-$C_{30}$ alkylene, and wherein the polymerized polysiloxane unit is the reaction residue of its corresponding dihydroxy compound. In a specific embodiment, the polydiorganosiloxane blocks are provided by repeating structural units of formula (14):

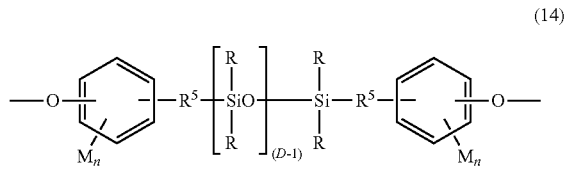

(14)

wherein R and D are as defined above. Each $R^5$ in formula (14) is independently a divalent $C_2$-$C_8$ aliphatic group. Each M in formula (14) may be the same or different, and may be a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ arylalkyl, $C_7$-$C_{12}$ arylalkoxy, $C_7$-$C_{12}$ alkylaryl, or $C_7$-$C_{12}$ alkylaryloxy, wherein each n is independently 0, 1, 2, 3, or 4.

Units of formula (14) may be derived from the corresponding dihydroxy polydiorganosiloxane (15):

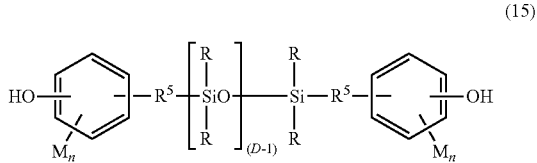

(15)

wherein R, D, M, $R^5$, and n are as described above. Such dihydroxy polysiloxanes can be made by effecting a platinum catalyzed addition between a siloxane hydride of formula (16):

(16)

wherein R and D are as previously defined, and an aliphatically unsaturated monohydric phenol.

In an embodiment, the polysiloxane-polycarbonate may comprise polysiloxane units, and carbonate units derived from bisphenol-A, e.g., the dihydroxy compound of formula (3) in which each of $A^1$ and $A^2$ is p-phenylene and $Y^1$ is isopropylidene. Polysiloxane-polycarbonates may have a weight average molecular weight of 2,000 to 100,000, specifically 5,000 to 50,000 as measured by gel permeation chromatography using a crosslinked styrene-divinyl benzene column, at a sample concentration of 1 milligram per milliliter, and as calibrated with polycarbonate standards.

The polysiloxane-polycarbonate can have a melt volume flow rate, measured at 300° C. under a load of 1.2 kg, of 1 to 50 cubic centimeters per 10 minutes (cc/10 min), specifically 2 to 30 cc/10 min. Mixtures of polysiloxane-polycarbonates of different flow properties may be used to achieve the overall desired flow property. In an embodiment, exemplary polysiloxane-polycarbonates are marketed under the trade name LEXAN® EXL polycarbonates, available from SABIC Innovative Plastics.

The sheet further comprises a fluorescent dye. The term "fluorescent" refers to the emission of light by the dye, after absorbing light radiation, at a defined wavelength (due to the Stokes shift). By comparison, a non-fluorescent dye does not absorb the energy and re-emit it at a defined wavelength, but as heat (i.e. a broad band of radiation).

Dispersed within the sheet is a dye compound of Formula (I) or (II) as described above, wherein each R and R' is independently selected from $C_1$-$C_{18}$ alkyl, substituted $C_1$-$C_{18}$ alkyl, $C_1$-$C_{18}$ alkoxy, substituted $C_1$-$C_{18}$ alkoxy, and halogen; each m is independently an integer from 0 to 5; and each k is independently an integer from 0 to 4. The term "dispersed" refers to the distribution of the dye within the thermoplastic polymer and is not intended to limit the means by which the dye is distributed within the polymer. In other words, the dye can be "dispersed" by means including dispersing, dissolving, doping, emulsifying, etc.

The sheet of the solar collector has an edge emission output of about 150 W/m² or greater when measured using a sheet of dimensions 60 mm×60 mm×3.2 mm and exposed to a radiation intensity of about 1000 W/m², including about 200 W/m² or greater, or 210 W/m² or greater. When measured, the sheet should have a smooth, high gloss surface; in other words, the surface should not be textured. The surface may have a 60 degree gloss generally greater than about 95. The term "sheet" should not be construed as limiting the method by which the thermoplastic part is manufactured. The sheet may be extruded, injection molded, or otherwise formed, as described further below. A sheet or plaque of the correct dimensions may be used to measure the edge emission output.

In particular embodiments, the sheet contains a dye compound of Formula (III), (IV), (V), or (VI).

If desired, additional fluorescent dyes may be included in the sheet. Exemplary dyes include the daylight fluorescent-type dyes that belong to the dye families known as rhodamines, fluoresceins, coumarins, naphthalimides, benzoxanthenes, perylenes, pyrenes, acridines, or a combination comprising at least one of the foregoing. Examples include luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3"",5""-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H-pyran; 1,1'-diethyl-2,2'-carbocyanine iodide; 3,3'-diethyl-4,4',5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene; chrysene; rubrene; coronene, or the like; perylene dyes such as those based on imido derivatives of perylene tetracarboxylic acid; or combinations comprising at least one of the foregoing dyes. Suppliers of fluorescent colorants include Radiant Color Company (Richmond, Calif.), Day-Glo Color Corp. (Cleveland, Ohio), Sun Chemical Co. (Cincinnati, Ohio). Sinloihi Co. Ltd. (Tokyo, Japan), Swada (London, England), Mikuni Color Works Ltd. (Himeji, Japan), Matsui International Co, Inc (Japan), Nippon Keiko Color Company (Japan). Specifically useful fluorescent dyes include those available under the following tradenames: Diaresin® dyes from Mitsubishi Chemical (Japan); Lumogen® dyes from BASF (Germany), Irgalite® and Maxilon® dyes from Ciba Specialty Chemicals (Germany), Macrolex® dyes from Lanxess (Germany), and Hostasol® dyes from Clariant. Typical commercially available fluorescent dyes of the above types include amino phthalate dyes such as Rhodamine BDC (C.I. 45,170), Rhodamine 6GDN extra (C.I. 45,160; Red 480), Rhodamine F5G (Red 482), Rhodamine FB (Red 540), and Rhodamine F3B (C.I. 45,175); naphthalimide derivatives such as Lumogen® F Blue 650; perylene derivatives such as Lumogen® F Red 305; Lumogen® F Yellow 083; Lumogen® F Violet 570; Lumogen® F Green 850; Macrolex® Fluorescent Yellow 10GN (C.I. Solvent Yellow 160:1); Macrolex® Red G; Irgalite® Violet M, Maxilon® Brilliant Flavine 10GFF, Maxilon® Black FBL-01, Maxilon® Black RM-01, Maxilon® Blue 5G, Maxilon® Blue 5G-01, Maxilon® Blue GRL/Pearl, Maxilon® Blue GRL Granulated, Maxilon® Blue GRL E, Maxilon® Blue M-G, Maxilon® Blue TRL Liquid, Maxilon® Golden Yellow GL Pearls, Maxilon® Navy FRL-02, Maxilon® Red GRL-01 Pearl, Maxilon® Red GRL-E, Maxilon® Red GRL Pearls, Maxilon® Red M-4GL, Maxilon® Yellow M-3RL, and Maxilon® Yellow M-4GL; Hostasol® Red 5B (Vat Red 41), Hostasol® Red GG (Solvent Orange 63), and Hostasol® Yellow 3G (Solvent Yellow 98); Fluorescent yellow F6PN and Yellow Y toner; Fluorescent Red 66; fluorescein; and 9-aminoacridine. A combination comprising at least one of the foregoing fluorescent dyes may be used. In an exemplary embodiment, fluorescent dyes useful herein include Lumogen® F Blue 650, Lumogen® Red 305, and Macrolex® Fluorescent Yellow 10GN. It will be understood that numerous fluorescent dyes are available commercially and are useful herein, and that therefore the foregoing list of fluorescent dyes should be considered exemplary, and not limiting to the dyes disclosed hereinabove. The fluorescent dye is generally dispersed completely throughout the sheet.

The fluorescent dye may be covalently bonded to a polymeric backbone to provide a polymer-supported fluorescent dye, and may also be referred to as dye conjugates. Such dye conjugates are useful to provide a fluorescent dye that is predispersed, i.e., one that is distributed throughout the polymer and which can provide a maximum fluorescence due to the more uniform dispersion. Dyes which are not so dispersed may aggregate or clump, and thereby decrease the effective loading of the dye based on the desired linear relationship between the fluorescent intensity and dye loading. Further, aromatic dyes, such as for example pyrene-based dyes, can when held proximate to one another form dimeric complexes ("excimers") that can have a shifted absorbance and/or fluorescent emission wavelength and intensity relative to the parent non-dimeric dye. Distributing the fluorescent dye along a polymer backbone by covalent bonding can, in addition to the advantages enumerated hereinabove, be used as a method to reduce or eliminate excimer formation. Fluorescent dyes that are useful for preparing dye conjugates include those having reactive functional groups capable of forming a covalent bond with a useful monomer or functional polymer or functional resin. Exemplary reactive groups provided by the fluorescent dye include phenolic hydroxy, aliphatic hydroxy, aromatic amine, aliphatic amine, thiols, carboxylic acid, and carboxylate esters. It will be understood that the foregoing list of reactive groups is meant to be exemplary, and should not be limited thereto.

Further functionalization of these functional fluorescent dyes, to provide reactive derivatives, can further increase the reactive usefulness of the fluorescent dye so functionalized. Reactive substituents can be formed by covalently reacting functional agents such as, for example, reactive derivatives of (meth)acrylic acid such as (meth)acryloyl chloride; carbonyl dihalides such as phosgene; thiocarbonyl dihalides such as thiophosgene; maleic anhydride; chloroformates including alkyl, aryl, or aralkyl chloroformates, epichlorohydrin; or the like; to the above functional dyes to provide suitable reactive groups. In an exemplary embodiment, useful functionalized fluorescent dyes include functional groups such as (meth)acrylates, (meth)acrylamides, N-hydroxysuccinimidyl (NHS) esters, isocyanates, isothiocyanates, maleimides, chloroformates, anhydrides, mixed anhydrides, epoxides, and the like. Polymeric backbone supports for such dyes can include linear polymers, crosslinked polymers, dendrimers, graft copolymers, block copolymers including two or more blocks, end group modified polymers, hyperbranched copolymers, telechelic oligomers, or the like. Useful backbone polymers typically includes poly(meth)acrylic homopolymers or copolymers including poly(meth)acrylates, poly(meth)acrylamides, and the like; poly(vinyl aromatic) polymers and copolymers, including polystyrenes, copolymers thereof, and the like; polyvinyl polymers such as poly(vinyl acetate) or poly(vinyl alcohol), copolymers thereof, and the like; poly(alkylene oxide)s, copolymers thereof, and the like. In an embodiment, the functionalized fluorescent dye is attached to a polymer by reaction of the functional dye with a complementarily functionalized polymer. In another embodiment, the functionalized fluorescent dye having a polymerizable end group such as a (meth)acrylate or epoxide can be copolymerized with other monomers or reactive oligomers to provide a polymer-supported fluorescent dye. Other polymeric backbones that may be used as backbone support include polyesters, polycarbonates, polyimides, carbohydrate materials including substituted or unsubstituted cellulosic materials, polysaccharides, dextrins, aminosugars, and the like; proteins; or a combination comprising at least one of the foregoing polymers. In an embodiment, the polymer-supported fluorescent dyes include fluorescent dyes incorporated into the polymeric backbone in an amount of 0.5 to 50 wt %, specifically 1 to 45 wt %, and more specifically 5 to 40 wt %, based on the total weight of the fluorescent dye and polymer backbone.

A fluorescent brightener can also be included with the fluorescent dye. Fluorescent brighteners include fluorescent compounds which, when combined with a dye having relatively low fluorescence, act to increase the intensity of the fluorescent emissions from the dye combination. In an embodiment, a fluorescent brightener is used in combination with a blue fluorescent dye. Exemplary fluorescent brighteners include those marketed under the tradename Uvitex® and available from Ciba Specialty Chemicals, or DIPHYL® and BLANKOPHOR® available from Lanxess. In a specific exemplary embodiment, a useful combination of a blue dye and fluorescent brightener includes Uvitex® OB, available from Ciba Specialty Chemicals, as fluorescent brightener. It will be understood that the foregoing fluorescent brightener is exemplary and should not be considered as limiting thereto.

When used, a fluorescent brightener may be included in an amount of from about 0.005 weight percent to about 25 weight percent, specifically from about 0.01 weight percent to about 20 weight percent, and more specifically from about 0.015 weight percent to about 15 weight percent, based on the total weight of the sheet it is in.

The fluorescent dye of Formula (I) or (II) is generally used in amounts of from about 0.001 weight percent to about 1 weight percent, particularly from about 0.005 weight percent to about 0.1 weight percent, and more particularly from about 0.02 weight percent to about 0.05 weight percent, based on the total weight of the sheet.

In the luminescent solar collector, a sheet or panel as described above is operatively connected to a light energy converter, such as a photovoltaic cell, or photocell. The photocell converts the light energy into electrical energy. Several different types of photocells may be used. Suitable bulk technology photocells include amorphous silicon cells, multicrystalline silicon cells, and monocrystalline silicon cells. Suitable thin film technology photocells include cadmium telluride cells, copper indium selenide cells, gallium arsenide or indium selenide cells, and copper indium gallium selenide cells. In specific embodiments, the photocell is a multicrystalline silicon photocell or a monocrystalline silicon photocell.

Generally, each type of photocell has a "sweet spot", or a range of wavelengths (light energy) which it converts most efficiently into electric energy. The photocell should be selected so that its sweet spot matches, as much as possible, the light emitted by the sheet of the LSC. For example, the sweet spot of a multicrystalline silicon photocell or a monocrystalline silicon photocell is from about 700 nanometers to about 1100 nanometers.

In addition to the components described hereinabove, the sheet may further include various other additives ordinarily incorporated with thermoplastic compositions of this type, with the proviso that the additives are selected so as not to adversely affect the desired properties of the thermoplastic composition. Mixtures of additives may be used. Such additives may be mixed at a suitable time during the mixing of the components for forming the thermoplastic composition.

Further non-limiting examples of additives that may be included in the sheet and/or the polymer layers include optical effects filler, antioxidant, heat stabilizer, light stabilizer, ultraviolet light absorber, plasticizer, mold release agent, lubricant, antistatic agent, flame retardant, anti-drip agent, gamma stabilizer, or a combination comprising at least one of the foregoing additives. Each of these additives can be present in amounts of from about 0.0001 to about 10 weight percent, based on the total weight of the sheet and/or layer the additive is in.

The sheet may be manufactured by methods generally available in the art. In particular, the dye compounds of Formula (I) or (II) can be easily incorporated into polycarbonate or poly(methyl methacrylate) polymers to give a uniform dye dispersion. For example, in one embodiment, in one manner of proceeding, powdered polycarbonate and fluorescent dye are first blended in a HENSCHEL-Mixer® high speed mixer. Other low shear processes including but not limited to hand mixing may also accomplish this blending. The blend is then fed into the throat of an extruder via a hopper. Alternatively, one or more of the components may be incorporated into the composition by feeding directly into the extruder at the throat and/or downstream through a sidestuffer. The fluorescent dyes of Formula (I) or (II) can be added either as a powder or as a solution in a suitable solvent. Generally, the dyes can be distributed within the polycarbonate using any means which accomplish the purpose, such as by dispersion. Additives may also be compounded into a masterbatch with a desired polymeric resin and fed into the extruder. The extruder is generally operated at a temperature higher than that necessary to cause the composition to flow. The extrudate is immediately quenched in a water batch and pelletized. The pellets, so prepared, when cutting the extrudate may be one-fourth inch long or less as desired. Such pellets may be used for subsequent molding, shaping, or forming. The sheet and/or polymer layers may be molded from the thermoplastic composition by a variety of means such as injection molding, extrusion, rotational molding, blow molding and thermoforming. In a specific embodiment, molding is done by injection molding.

The following examples are provided to illustrate the luminescent solar collectors of the present disclosure. The examples are merely illustrative and are not intended to limit devices made in accordance with the disclosure to the materials, conditions, or process parameters set forth therein.

EXAMPLES

Equipment

During compound synthesis, the compounds of Formula (I) were separated using a liquid chromatograph-mass spectrometer (LC-MS) system comprising a liquid chromatograph and a Quattro® Ultima Pt mass spectrometer. An Xterra® C18 (50 mm×4.6 mm; 5 microns) column was used for separating the components by liquid chromatography.

Proton NMR spectra were measured using a 300 MHz Bruker® NMR spectrometer. $CDCl_3$ was used as the recording solvent.

The absorption spectra and extinction coefficient were measured using a double beam Perkins-Elmer® Lambda 900 UV-Vis-NIR spectrophotometer. Measurements were made in toluene or $CHCl_3$.

The emission spectra and quantum yield were measured with a Horiba Jobin Yvon Fluorolog®-3 fluorescence spectrophotometer, Model No: FL3-211. Measurements were made in toluene.

The decomposition temperature was measured by differential scanning calorimetry (DSC) using a Q10 series machine from TA Instruments. The increase in temperature was 10° C./minute.

A solar simulator (PET SS200B simulator with a class B xenon lamp) illuminated each chip under AM1 illumination (air mass 1.5 spectral curve) and a power of 1000 W/m$^2$ for an area of 200 mm×200 mm. A calibrated Ocean Optics HD200 spectrophotometer (range 380 nm to 1100 nm, resolution of 0.5 nm) with an optical fibre probe and attached collimating lens was used to determine the intensity of the edge emission per area (W/m$^2$). The spectrophotometer was calibrated over 300 nm to 1050 nm using a bulb with a 3100K color temperature.

Example 1

Synthesis of Intermediate 1,6,7,12-tetrachloroperylene-3,4,9,10-tetradicarboxydianhydride (2 grams, 3.8 mmol) and o-phenylenediamine (1.85 grams, 17.1 mmol) were placed into a 100 mL round bottom flask, and 30 mL propionic acid was added. The mixture was stirred at 140° C. for 6 hours, then cooled to 80-90° C. and filtered hot using a glass sinter funnel. The intermediate product was then washed with 15 mL warm propionic acid followed by a large excess of water. Next, the intermediate product was dried under suction, then in an air oven at 80° C. for 10 hours. The yield of the intermediate product was 2.4 grams (~62%). These steps were run multiple times to obtain a quantity of intermediate product for use in the subsequent Examples as described below.

Example 2

Synthesis of Formulas (III) and (IV)

The intermediate product synthesized in Example 1 (3 grams, 4.4 mmol), nonyl phenol (5.85 grams, 26.4 mmol) and potassium carbonate (3.65 grams, 26.4 mmol) were added to 60 mL N-methylpyrrolidone. The reaction mixture was stirred at 150° C. for 24 hours, then cooled to room temperature. The reaction mixture was treated with chilled 10 mL concentrated HCl in an ice bath until evolution of gas ceased. The precipitate obtained was filtered through a glass sinter funnel, washed repeatedly with water, and then washed with 30 mL of methanol five times. The yield was 2.1 grams (77% pure compound). It was then purified using silica gel column chromatography using 10-30% dichloromethane-hexane mixture through gradual elution. The final yield was a 0.6 gram mixture of isomers Formula (III) and Formula (IV).

$^1$H-NMR for Formulas (III) and (IV) (CDCl$_3$): 8.56-8.42 (m, 4H), 7.83-7.79(m, 2H), 7.50-7.43 (m, 4H), 7.33-7.20(m, 12H), 7.01-6.84(m, 6H),1.85-1.56(m, 16H), 1.33-1.27(m, 20H), 0.91-0.43(m, 36H).

Example 3

Synthesis of Formula (V) and (VI)

The intermediate product synthesized in Example 1 (5 grams, 7.4 mmol), 4-tert-octyl phenol (9.08 grams, 44 mmol) and potassium carbonate (6.07 grams, 44 mmol) were taken in 150 mL N-methylpyrrolidone. The reaction mixture was stirred at 140° C. for 24 hours, then cooled to room temperature. The reaction mixture was treated with chilled 10 mL concentrated HCl in an ice bath until evolution of gas ceased. The precipitate obtained was filtered through a glass sinter funnel, washed repeatedly with water, and then washed with 30 mL of methanol five times. It was then purified using silica gel column chromatography using 10-30% dichloromethane-hexane mixture through gradual elution. The final yield was a 2.0 gram mixture of isomers Formula (V) and Formula (VI).

$^1$H-NMR for Formulas (V) and (VI) (CDCl$_3$): 8.51-8.37 (m, 4H), 7.79-7.78(m, 2H), 7.49-7.45 (m, 3H), 7.33-7.20(m, 13 H), 7.01-6.84(m, 6H),1.84-1.76(m, 8H), 1.65-1.55 (m, 24H), 0.89-0.83(m, 36H).

Example 4

Synthesis of Formula (VII) and (VIII)

The intermediate product synthesized in Example 1 (5 grams, 7.4 mmol), 4-tert-butyl phenol (6.66 grams, 44 mmol) and potassium carbonate (6.07 grams, 44 mmol) were taken in 150 mL N-methylpyrrolidone. The reaction mixture was stirred at 140° C. for 24 hours, and then cooled to room temperature. The reaction mixture was treated with chilled 10 mL concentrated HCl in an ice bath until evolution of gas ceased. The precipitate obtained was filtered through a glass sinter funnel, washed repeatedly with water, and then washed with 30 mL of methanol five times. It was then purified using silica gel column chromatography using 10-30% dichloromethane-hexane mixture through gradual elution. The final yield was a 1.70 gram mixture of isomers Formula (VII) and Formula (VIII).

$^1$H-NMR for Formulas (VII) and (VIII) (CDCl3): 8.57-8.15(m, 4H), 7.86-7.47(m, 1H), 7.49-7.47(m, 3H), 7.3-7.26 (m, 14H), 6.96-6.85(m, 6H), 1.34(m, 36H tert-CH$_3$ group proton).

Comparison with Other Compounds

The compounds of Formulas (III) through (VIII) were compared to the following comparative compounds: terrylene diimide, Violanthrone-79, and Vat Green-1. These compounds are shown below:

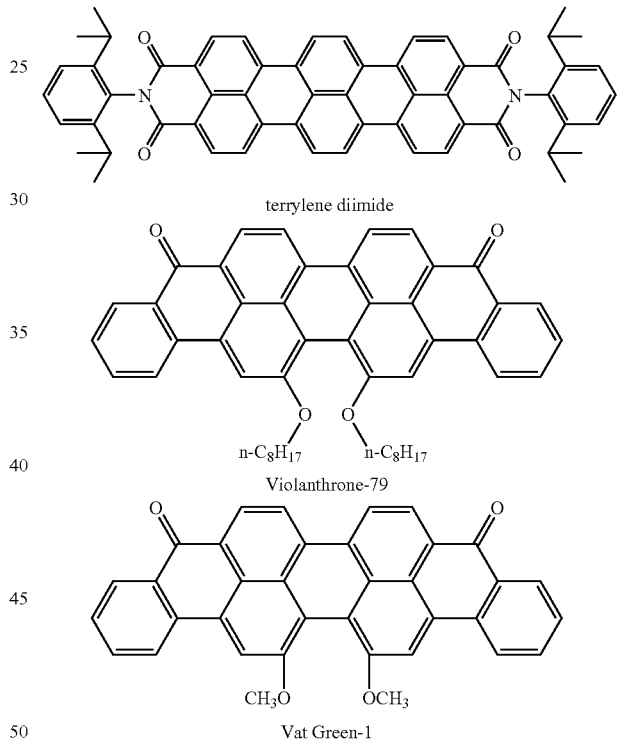

terrylene diimide

Violanthrone-79

Vat Green-1

The following Table 1 shows the photophysical properties of compounds of Formulas (III) through (VIII) and the three comparative compounds. The quantum yield was measured in chloroform:

TABLE 1

| Compound | $\lambda_{abs}$ (nm) | Extinction coefficient (L/cm · mol) | $\lambda_{emission}$ (nm) | Decomposition Temperature (° C.) DSC | Quantum Yield |
|---|---|---|---|---|---|
| Formulas (III) & (IV) | 630 | 63700 | 666 | >378 | 1 |
| Formulas (V) & (VI) | 633 | 68039 | 667 | >350 | 0.96 |

TABLE 1-continued

| Compound | $\lambda_{abs}$ (nm) | Extinction coefficient (L/cm · mol) | $\lambda_{emission}$ (nm) | Decomposition Temperature (° C.) DSC | Quantum Yield |
|---|---|---|---|---|---|
| Formulas (VII) & (VIII) | 630 | 61200 | 666 | >358 | 0.96 |
| Terrylene diimide | 650 | 90000 | 680 | 357 | 0.54 |
| Violanthrone-79 | 620 | 36246 | 720 | 350 | 0.36 |
| Vat Green-1 | 619 | 40974 | 720 | >350 | 0.32 |

As seen here, the compounds of Formulas (III) through (VIII) have much higher quantum yields than the comparative compounds; they are all greater than 95%. They absorb in the desired range (600-650 nm) and emit in the desired range (>650 nm).

Example 5

The three isomeric mixtures of Formulas (III) & (IV), Formulas (V) & (VI), and Formulas (VII) & (VIII) were then molded into plaques and tested for their edge emission output, as were two of the comparative compounds, Violanthrone-79 and terrylene diimide.

The plaques were formed from a mixture of 1 kg polycarbonate and approximately 100 milligrams dye. The polycarbonate was a bisphenol-A homopolycarbonate having a weight average molecular weight of 60,000 versus polystyrene standards and a polydispersity of 2.1 to 2.3. The polycarbonate and dye were placed in a zip-lock polyethylene bag and shaken vigorously for about 3-4 minutes. The mixture was then extruded to produce pellets. The extruded pellets were dried in an oven at 120° C. for about 6 hours, then molded using an LTM-Demag molding machine in square plaques of 60 mm×60 mm, with 3.2 mm thickness.

The plaques were placed under a solar simulator (1000 W/m²) and the edge emission output was measured. The results are shown in Table 2. The dyes of Formulas (III) & (IV), Formulas (V) & (VI), and Formulas (VII) & (VIII) all had a much higher edge emission than the comparative compounds. The dyes of Formulas (VII) & (VIII), were the lowest of the three isomeric mixtures.

TABLE 2

| Compound | Edge Emission (W/m²) |
|---|---|
| Terrylene diimide | 80 |
| Violanthrone-79 | 80 |
| Formulas (III) & (IV) | 221 |
| Formulas (V) & (VI) | 244 |
| Formulas (VII) & (VIII) | 203 |

The dyes, luminescent solar collectors, and processes of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A fluorescent dye selected from the group consisting of Formula (I) and Formula (II):

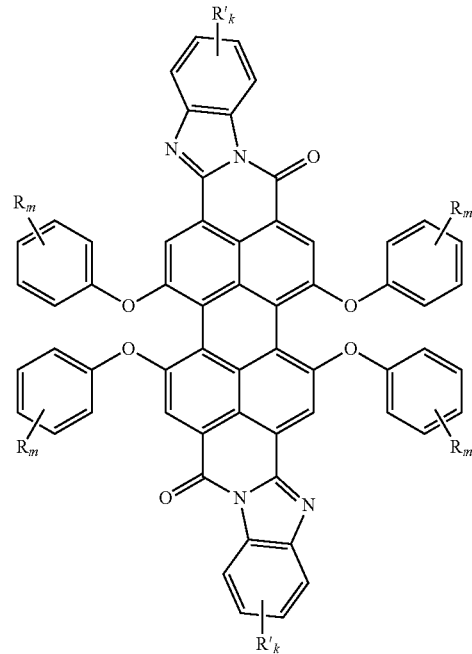

Formula (I)

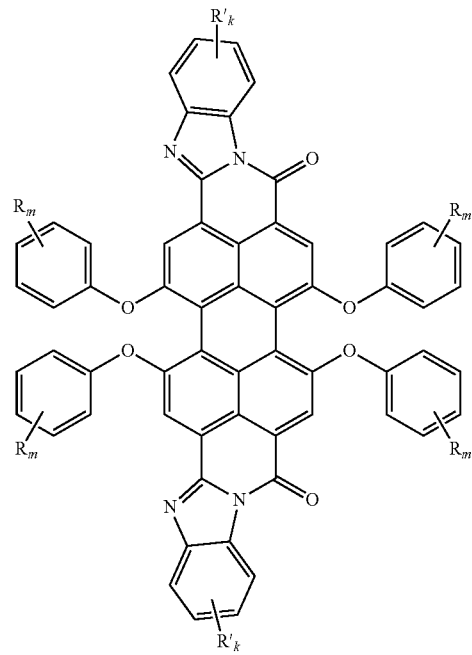

Formula (II)

wherein each R and R' is independently selected from $C_8$-$C_{18}$ alkyl, substituted $C_8$-$C_{18}$ alkyl, $C_8$-$C_{18}$ alkoxy, substituted $C_8$-$C_{18}$ alkoxy, and halogen; m represents the number of R substitutents on each phenoxy ring, wherein each m is independently an integer from 0 to 5; and k represents the number of R' substituents on each benzimidazole group, wherein each k is independently an integer from 0 to 4; and wherein each phenoxy ring is substituted in only the para position with an R group independently selected from $C_8$-$C_{18}$ alkyl.

2. The fluorescent dye of claim 1, wherein the four R groups in the para position are the same.

3. A fluorescent dye selected from the group consisting of Formula (I) and Formula (II):

Formula (I)

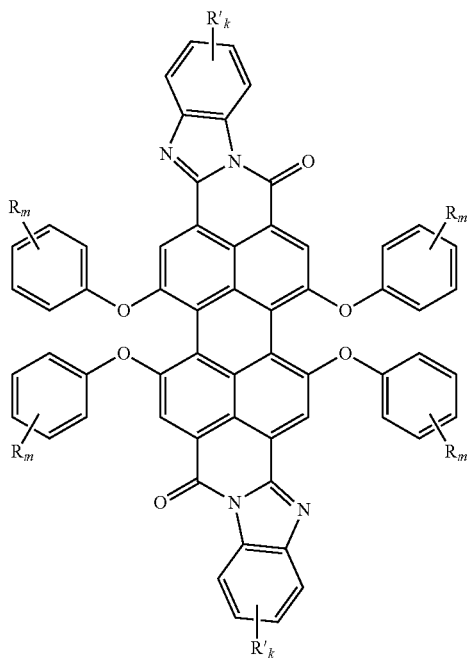

Formula (II)

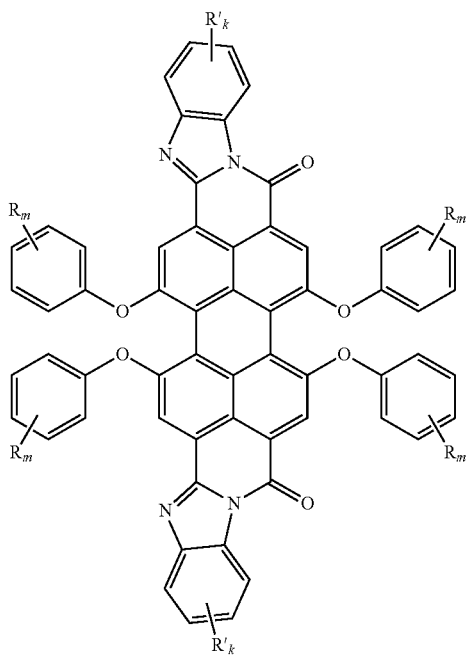

wherein each R and R' is independently selected from $C_8$-$C_{18}$ alkyl, substituted $C_8$-$C_{18}$ alkyl, $C_8$-$C_{18}$ alkoxy, substituted $C_8$-$C_{18}$ alkoxy, and halogen; m represents the number of R substitutents on each phenoxy ring, wherein each m is independently an integer from 0 to 5; and k represents the number of R' substituents on each benzimidazole group, wherein each k is independently an integer from 0 to 4; and wherein the fluorescent dye has a quantum yield of about 80% or greater.

4. The fluorescent dye of claim 3, wherein the fluorescent dye has a quantum yield of 90% or greater.

5. The fluorescent dye of claim 3, wherein the fluorescent dye has a quantum yield of 95% or greater.

6. A fluorescent dye selected from the group consisting of Formula (I) and Formula (II):

Formula (I)

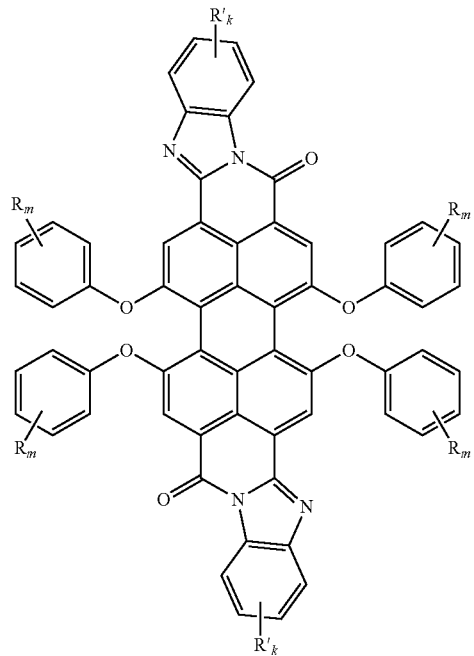

Formula (II)

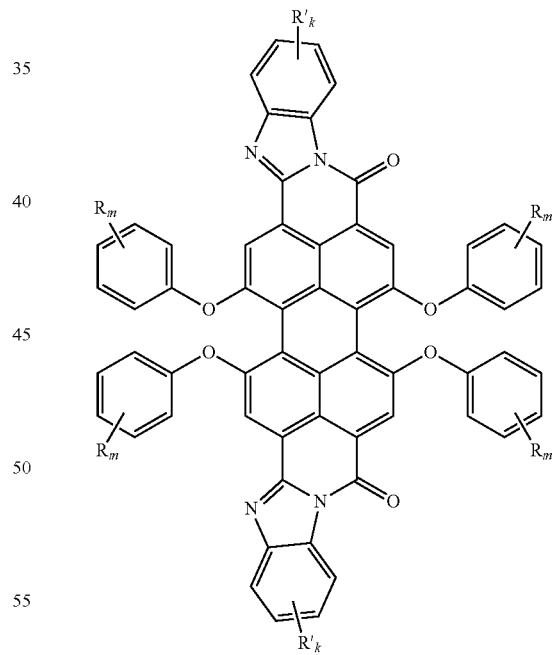

wherein each R and R' is independently selected from $C_8$-$C_{18}$ alkyl, substituted $C_8$-$C_{18}$ alkyl, $C_8$-$C_{18}$ alkoxy, substituted $C_8$-$C_{18}$ alkoxy, and halogen; m represents the number of R substitutents on each phenoxy ring, wherein each m is independently an integer from 0 to 5; and k represents the number of R' substituents on each benzimidazole group, wherein each k is independently an integer from 0 to 4; and wherein the fluorescent dye has a maximum absorption wavelength of from about 600 nm to 650 nm and has a maximum emission wavelength of 650 nm or greater.

7. A fluorescent dye selected from the group consisting of Formulas (III), (IV), (V), and (VI):
Formula (III)
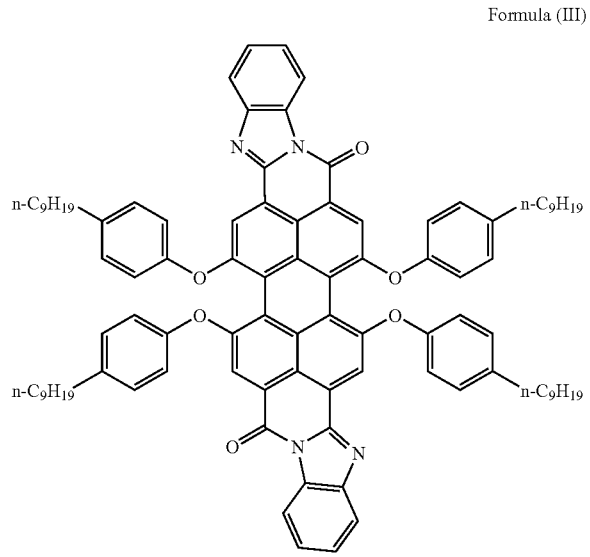
Formula (IV)
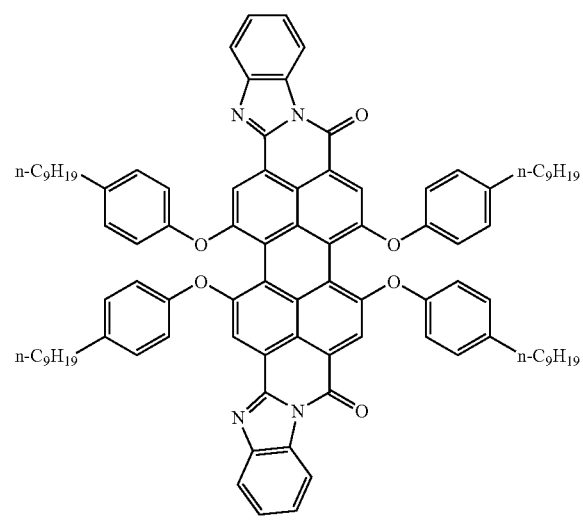
Formula (V)
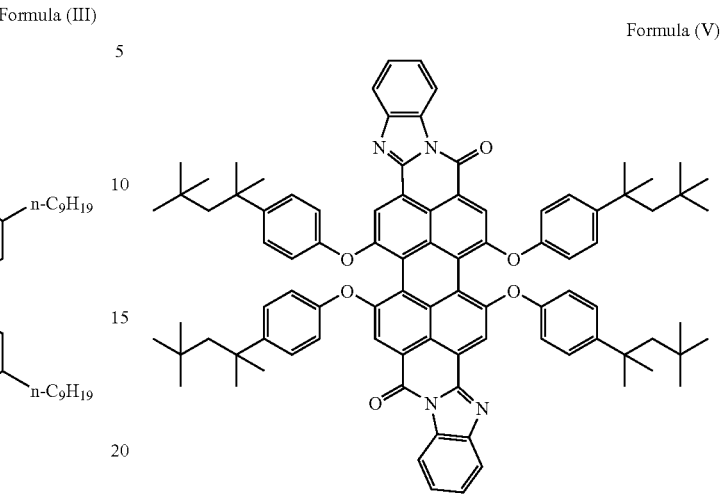
Formula (VI)
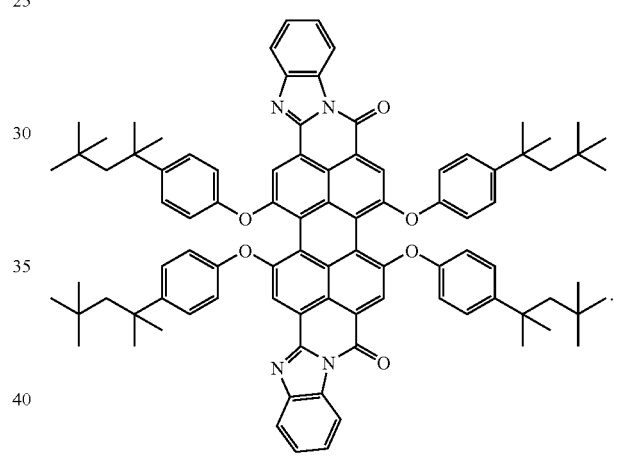
* * * * *